(12) United States Patent
Urschey et al.

(10) Patent No.: US 11,643,384 B2
(45) Date of Patent: May 9, 2023

(54) STABILIZATION OF COMPOSITIONS COMPRISING QUATERNARY TRIALKYLALKANOLAMINE HYDROXIDE

(71) Applicant: KURITA WATER INDUSTRIES LTD., Tokyo (JP)

(72) Inventors: Michael Urschey, Duessledorf (DE); Tim Rudolph, Duessledorf (DE)

(73) Assignee: KURITA WATER INDUSTRIES LTD., Tokyo (JP)

( * ) Notice: Subject to any disclaimer, the term of this patent is extended or adjusted under 35 U.S.C. 154(b) by 386 days.

(21) Appl. No.: 16/961,231

(22) PCT Filed: Apr. 26, 2018

(86) PCT No.: PCT/JP2018/016949
§ 371 (c)(1),
(2) Date: Jul. 9, 2020

(87) PCT Pub. No.: WO2019/207701
PCT Pub. Date: Oct. 31, 2019

(65) Prior Publication Data
US 2021/0061754 A1  Mar. 4, 2021

(51) Int. Cl.
| | | |
|---|---|---|
| *C07C 213/10* | (2006.01) | |
| *C02F 5/12* | (2023.01) | |
| *C10G 75/02* | (2006.01) | |
| *C10G 75/04* | (2006.01) | |
| *C23F 11/14* | (2006.01) | |
| *G03F 7/42* | (2006.01) | |

(52) U.S. Cl.
CPC ............. *C07C 213/10* (2013.01); *C02F 5/12* (2013.01); *C10G 75/02* (2013.01); *C10G 75/04* (2013.01); *C23F 11/141* (2013.01); *G03F 7/425* (2013.01); *C02F 2303/08* (2013.01)

(58) Field of Classification Search
None
See application file for complete search history.

(56) References Cited

U.S. PATENT DOCUMENTS

| | | | | |
|---|---|---|---|---|
| 2,667,487 A | * | 1/1954 | Firestone | C07D 473/08 544/272 |
| 2,778,789 A | * | 1/1957 | McNeill | C25D 11/00 205/106 |
| 3,399,146 A | * | 8/1968 | Clyde | C11D 1/002 564/453 |
| 5,209,858 A | | 5/1993 | Heinsohn et al. | |
| 7,279,089 B2 | | 10/2007 | Vercammen | |
| 8,177,962 B2 | | 5/2012 | Koizumi et al. | |
| 8,728,392 B2 | * | 5/2014 | Mori | C23F 11/10 252/392 |
| 9,670,137 B2 | | 6/2017 | Ferguson | |
| 2007/0193708 A1 | | 8/2007 | Broucek et al. | |
| 2014/0361217 A1 | | 12/2014 | Moonen et al. | |
| 2017/0121275 A1 | | 5/2017 | Moonen et al. | |
| 2017/0306504 A1 | * | 10/2017 | Moloney | C22C 38/002 |

FOREIGN PATENT DOCUMENTS

| | | |
|---|---|---|
| EP | 2797873 | 11/2014 |
| JP | 2004067548 | 3/2004 |

OTHER PUBLICATIONS

"International Search Report (Form PCT/ISA/210) of PCT/JP2018/016949," dated Jan. 7, 2019, pp. 1-2.

* cited by examiner

Primary Examiner — John J Figueroa
(74) Attorney, Agent, or Firm — JCIPRNET

(57) ABSTRACT

A composition comprising a) a quaternary trialkylalkanolamine hydroxide and b) at least one diamine as component b), which is selected from the group consisting of 1-amino-4-methylpiperazine, 1,2-diaminopropane and mixtures thereof.

14 Claims, No Drawings

STABILIZATION OF COMPOSITIONS COMPRISING QUATERNARY TRIALKYLALKANOLAMINE HYDROXIDE

FIELD OF THE INVENTION

The invention relates to a stabilized composition of a quaternary trialkylalkanolamine hydroxide, in particular of choline hydroxide, to the use of such compositions and to a method for stabilizing a quaternary trialkylalkanolamine hydroxide.

BACKGROUND OF THE INVENTION

Compositions of quaternary trialkylalkanolamines have found a broad field of application. A typical member of quaternary trialkylalkanolamine is choline, i.e. 2-(hydroxyethyl)trimethylammonium of chemical formula $(CH_3)_3N^+(CH_2)_2OHX^-$, where $X^-$ is a counterion, such as chloride, hydroxide, citrate, tartrate or hydrogen tartrate.

Quaternary trialkylalkanolamine hydroxides such as choline hydroxide are strong organic bases suitable for many uses. Compositions comprising choline hydroxide are versatile in connection with electronic applications, such as positive photoresists developing agents, for stripping photoresists, anisotropic etching agents or washing agents for silicon wafers.

Further, choline hydroxide can be used in oil refinery and petrochemical applications for neutralization of acidic species, dissolution of ammonium salts, such as ammonium sulfide, ammonium sulfate and ammonium chloride and reducing or prevention of deposits of the same. The processes in oil refinery and petrochemical applications are e.g. hydro-treating, hydro-cracking, catalytic reforming or catalytic cracking. In such processes, ammonium chloride, ammonium sulfate and ammonium sulfides are generated and cause fouling and corrosion issues of the equipment. Choline hydroxide is injected into the process flow and converts ammonium chloride, ammonium sulfate and ammonium sulfides into non-corrosive and non-depositing components (see e.g. U.S. Pat. No. 7,279,089).

Apart from that choline hydroxide can be used as corrosion inhibitor in water steam cycles and in catalytic refining of crude oil (see U.S. Pat. No. 8,177,962).

A common problem of compositions of quaternary trialkylalkanolamine hydroxides such as choline hydroxide, in particular of aqueous solutions thereof, is a gradual decomposition of the quaternary trialkylalkanolamine hydroxide resulting in discoloration of such compositions. In particular, concentrated solutions of quaternary trialkylalkanolamine hydroxides become yellow and finally orange and develop precipitates within a short period of time. This is unwanted as it compromises product quality and usability, as well as the useful lifetime of products. Excessive discoloration may be accompanied by formation of insoluble matter being present in the solutions, posing additional problems like dosing equipment fouling.

The discoloration is caused mainly by two mechanisms, namely decomposition of the quaternary trialkylalkanolamine hydroxide by Hofmann elimination and oxidation/autoxidation reactions. Decomposition and color formation is accelerated by increasing concentration of the quaternary trialkylalkanolamine hydroxide in the composition, increasing temperature and exposure to air/oxygen. While oxidation/autoxidation can be at least partially prevented by using antioxidants, it is not possible so far to avoid Hofmann degradation, which is the main cause of discoloration.

Several approaches are known in the prior art to delay color formation in compositions of quaternary trialkylalkanolamine hydroxides and to stabilize the compositions in particular against discoloration.

According to a first approach, less concentrated solutions of the quaternary trialkylalkanolamine hydroxide may be used. While this approach somewhat delays the color formation, less concentrated solutions make it necessary to employ a greater amount which causes higher logistics, handling and transport costs, which is undesired.

According to a second approach, the compositions of the quaternary trialkylalkanolamine hydroxide are stored at low temperatures. While this approach is effective, especially at temperatures approaching 5° C. and lower (close to the freezing point of water), it is not at all practical due to increased energy and handling costs associated with cooling large amounts of material constantly. Moreover, in oil refinery and petrochemical applications, this is completely out of scope as process treatment products are usually stored outside in the plants without any access to temperature control.

According to a third approach, nitrogen or other inert gas blanketing is applied in order to reduce dissolved oxygen contents in the solution and hence oxidation reactions. However, constant nitrogen blanketing of storage vessels is costly and only removes a part of the problem, not the Hofmann elimination. Also, nitrogen blanketing is impractical in many refinery and petrochemical processes, since small product containers may need to be moved frequently.

In chemical industry, however, the dominant approach for stabilizing compositions of quaternary trialkylalkanolamine hydroxides, such as choline hydroxide, involves the use of chemical stabilizers in order to avoid decomposition/discoloration. Many stabilizing compounds are described and/or used in the prior art, most of them belonging to the chemical groups of carbonyl scavengers, oxygen scavengers/antioxidants and reducing agents. Carbonyl scavengers act by chemically binding the acetaldehyde formed by the Hofmann elimination before it can react to form a dimer, oligomer or polymer. Antioxidants/oxygen scavengers act by removing residual dissolved oxygen from the solutions and by terminating oxidation reactions. Strong reducing agents act by destructively reducing the aldehydes formed in the Hofmann elimination to form inactive compounds.

The use of strong reducing agents, such as sodium sulfite and sodium dithionite has been described e.g. in EP 2797873, US 2014/0361217 and US 2017/0121275. These references relate to a method for the production of choline hydroxide, wherein a stabilizer of a dithionite salt or a dialkylhydroxylamine is added during the production of choline hydroxide, and a second stabilizer of a dithionite salt or a dialkylhydroxylamine may be added to the aqueous solution containing choline hydroxide. However, the use of these reducing agents is not suitable in refinery and petrochemical applications because sodium acts as a catalyst poison in many processes relevant to this industry. Also, salt stabilizers may form undesirable sediments, especially at high concentrations.

US 2007/0193708 relates to a method for the stabilization of aqueous solutions of choline hydroxide by using a stabilizer selected from sodium borohydride and choline sulfite. However, the use of these compounds is generally not desirable due to their properties as reproductive toxins.

U.S. Pat. No. 9,670,137 relates to a method for the stabilization of choline hydroxide using an alkyl hydroxylamine, a hydrazine or hydrazide compound, in particular with a hydrazine or hydrazide having a hydroxylamine substituent. However, use of these compounds is generally discouraged since hydrazine itself and many hydrazine derivatives are carcinogenic. Therefore, the use of hydrazine is regulated restrictively in Europe.

EP 2797873 describes primary oligo amines, such as ethylenediamine (EDA) and diethylenetriamine (DETA) as stabilizing agents for choline hydroxide solutions. However, these compounds are not sufficiently effective under demanding conditions. Also, when used in refinery and petrochemical processes, EDA will form scaling and corrosive hydrochloride salts, which is undesirable.

EP 2797873 also mentions alkylhydroxylamines, such as N,N-diethylhydroxylamine (DEHA) in choline hydroxide solutions. While showing a reasonable efficiency, their activity is still not high enough for the stabilization of concentrated choline hydroxide solutions under demanding temperature conditions. When used as an oxygen scavenger, DEHA tends to form decomposition products such as diethylamine, acetaldehyde or acids, such as acetic acid, which are undesirable in refinery and petrochemical systems due to their corrosive nature. Hence, the usefulness of DEHA is limited.

Various antioxidants mainly belonging to the class of hindered phenols are known, for example methoxyphenoles, in particular 4-methoxyphenole (MEHQ). Such antioxidants are also described in EP 2797873. However, they do not show sufficient efficiency when used alone. This is due to the fact that the main color formation route is the Hofmann elimination, which is not alleviated by antioxidants.

U.S. Pat. No. 5,209,858 relates to the stabilization of aqueous solutions of choline hydroxide against discoloration comprising the addition of an unsubstituted hydroxyammonium salt.

Also, commercially available choline hydroxide solutions are frequently stabilized by hydroxylamine and its salts. However, the use of hydroxylamine is disadvantageous for at least two reasons. First, hydroxylamine is carcinogenic, and second it presents a significant explosion hazard when used as free base. To overcome this limitation, hydroxylamine salts, such as hydroxylamine sulfate (HAS) are frequently used, but their use causes secondary problems as well. Moreover, HAS and other salts are also carcinogenic. Further, their use as stabilizers of choline hydroxide solutions consumes valuable active material by an acid base reaction. Moreover, they are still subject to explosives regulations. Hence, the use of these compounds is discouraged.

While this approach is most dominant in industrial use of choline hydroxide, it has still limited applicability, scope and efficiency for the reasons outlined above.

To sum up, many stabilizer compounds for choline hydroxide solutions are described in the art. However, none of them work satisfactory, in particular under demanding temperature conditions, e.g. conditions occurring in oil refinery and petrochemical processes. This is because the stabilized compositions either form deposits or are corrosive when used in refinery and petrochemical processes or still tend to discoloration and formation of deposits at prolonged storage. Others require CMR-compounds, such as hydrazine, hydroxylamine, which is also not desirable.

It is, therefore, an object of the present invention to provide stabilized compositions comprising a quaternary trialkylalkanolamine hydroxide, in particular choline hydroxide, which overcomes at least some of the aforementioned disadvantages. In particular, the compositions should be stable at elevated temperatures and/or at high concentrations of the quaternary trialkylalkanolamine hydroxide without need for blanketing with nitrogen. Moreover, the compositions should preferably not require CMR-compounds, such as hydrazine or hydroxylamin. In particular, the compositions should be suitable for use in refinery and petrochemical processes.

SUMMARY OF THE INVENTION

The invention is based on the finding that the compounds 1-amino-4-methylpiperazine, 1,2-diaminopropane, either alone or as their mixtures, stabilize compositions comprising quaternary trialkylalkanolamine, in particular N,N,N-trimethyl-hydroxyethyl-ammonium hydroxide.

In particular, it was found that mixtures of stabilizing compounds in compositions comprising quaternary trialkylalkanolamine, in particular N,N,N-trimethyl-hydroxyethyl-ammonium hydroxide, satisfy the conditions demanded above. These mixtures offer the advantages of significantly improved performance at the lowest possible dosage levels of the stabilizing compound.

Therefore, a first aspect of the invention relates to compositions comprising
  a) a quaternary trialkylalkanolamine hydroxide and
  b) at least one compound b), which is selected from the group consisting of 1-amino-4-methylpiperazine, 1,2-diaminopropane and mixtures thereof.

The composition according to the invention and the special embodiments thereof described hereinafter is advantageous with respect to one or more of the following points:
  In the composition, the quaternary trialkylalkanolamine hydroxide is more stable compared to prior art.
  The composition does not need inert gas blanketing or temperature controlled storage.
  The composition is more stable at rather high storage temperatures, for example at 40-60° C., for prolonged periods of time.
  The composition does not require compounds, which are known or believed to be carcinogenic, mutagenic or toxic for reproduction (CMR-compounds), such as hydrazine, hydroxylamine or boron compounds.
  The composition has no negative impact on oil refinery and petrochemical processes, since the composition is free of catalyst poisons, such as alkali metals.
  A mixture of components b) or a mixture of at least one component b) and at least one component c) or a mixture of components c) shows synergistic action for the stabilization of compositions comprising the quaternary trialkylalkanolamine hydroxide, e.g. N,N,N-trimethyl-hydroxyethyl-ammonium hydroxide, i.e. the composition is more stable than it would have been expected from the individual compounds used for stabilization of quaternary trialkylalkanolamine hydroxide.

The invention also relates to the use of the composition for preventing fouling or corrosion of metal parts in oil refinery or petrochemical processes.

The invention also relates to the use of the composition for preventing fouling or corrosion in water/steam cycles, e.g. water/steam cycles of power plants.

The invention also relates to the use of the composition as a basic process chemical, in particular in as a basic chemical in a process, which requires the use of a strong organic base, for example in the preparation of electronics, where the composition is used as a positive photoresist developing agent, as an anisotropic etching agent or as a washing agent for silicon wafers.

The invention also relates to a method for stabilizing a quaternary trialkylalkanolamine hydroxide which comprises adding a component b) as defined herein to a composition of a quaternary trialkylalkanolamine hydroxide.

A further aspect of the invention relates to the use of a component b) as defined herein for stabilizing a composition of a quaternary trialkylalkanolamine hydroxide.

DETAILED DESCRIPTION OF THE INVENTION

Stabilizing compounds in the sense of the invention are compounds capable to stabilize component a). That means such compounds prevent or minimize degradation and decomposition of component a). Compositions comprising component a) and stabilizing compounds remain clear and colorless. Discoloration of said composition does not occur or only with a significant delay.

Component b) may be used as a sole stabilizer of compositions comprising component a). Generally, it is possible to use component b) as prestabilizer or poststabilizer. In one embodiment of the invention, component b) is used as prestabilizer of compositions comprising component a). In a preferred embodiment of the invention, component b) is used as poststabilizer of composition comprising component a).

In the sense of the invention, prestabilization refers to any stabilizer known in prior art, which is added before, during, and/or after production of quaternary trialkylalkanolamine hydroxide. If the stabilizer is added after formation of the quaternary trialkylalkanolamine hydroxide, the stabilizer is added as soon as the reaction is completed or at the latest one day after the quaternary trialkylalkanolamine hydroxide is formed. Said prestabilization may be achieved by any chemical compound or combinations thereof known in the prior art or by component b) as defined herein.

In the terms of the invention, poststabilization refers to the use of additional stabilizers being added to prestabilized compositions comprising quaternary trialkylalkanolamine hydroxide. The inventive stabilizing component b) or stabilizing mixtures thereof are added after the prestabilization process is completed. Preferably, the present invention refers to a poststabilization process. Thus, component b) refers preferably to poststabilizing compounds.

The above-referred composition, comprising components a) and b) is hereinbelow referred to as "inventive composition".

The compound 1,2-diaminopropane is also known as propane-1,2-diamine, which has the CAS No. 78-90-0. The compound 1-amino-4-methylpiperazine has the CAS No. 6928-85-4.

In the sense of the invention, the terms choline hydroxide and N,N,N-trimethyl-hydroxyethyl-ammonium hydroxide are used synonymously and have the chemical formula: $[(CH_3)_3NCH_2CH_2OH]^+OH^-$.

Here and hereinafter, the expression "aqueous composition" is taken to mean an aqueous composition, which comprises component a) and at least one component b) or mixtures thereof in dissolved form, optionally in addition to impurities.

The inventive composition is in particular an aqueous composition.

The composition comprising quaternary trialkylalkanolamine, in particular choline hydroxide is stabilized with component b). In particular, it is stabilized with a sole component b) (stabilizer) or a combination of components (b).

Thus, in the inventive composition a minimal or no development of heavy/dark color of the composition is to be expected. Additionally, the formation of precipitates is also reduced or eliminated. Stable, clear color and reduced precipitation may be due, at least in part, to minimization of the Hofmann elimination reaction in addition to minimization of oxidation, autoxidation, and/or other degradation reactions.

The concentration of component a) in the composition may influence the amount of degradation (e.g., color formation). For example, compositions comprising component a) having a low concentration of component a) (e.g., in the order of about 10-15% choline hydroxide) may hardly develop any color over time (e.g., for weeks or even months). On the other hand, compositions comprising a high concentration of component a) (e.g., about 45% choline hydroxide in the solution) can develop dark color very quickly (e.g., in the order of about one day). Thus, the component b) described herein is effective at both low and high amounts of component a).

For example, component b) is effective for compositions containing a concentration of component a), in particular choline hydroxide at 45% component a) or greater, 40% component a) or greater, 25% component a) or greater, 10% component a) etc., based on the total concentration of the composition.

In one embodiment, the concentration of component a) of the inventive composition is of 5 to 60% by weight, preferably of 20 to 60% by weight, especially 40 to 50% by weight, based on the total weight of the composition.

According to the invention, the concentration of component b) of the inventive composition is preferably of up to 3% by weight, more preferably of up to 1% by weight, based on the total weight of the composition. Preferably, the concentration of component b) in the inventive composition is 0.1 to 3% by weight, more preferably 0.1 to 2% by weight, especially 0.1 to 1% by weight based on the total weight of the composition.

In a preferred embodiment, the concentration of component b) in the inventive composition is of 0.1 to 2% by weight, based on a composition comprising 40 to 50% by weight of component a).

In a more preferred embodiment, the total concentration of component b) and prestabilizing compounds is at the most 3% by weight, based on the total weight of the inventive composition.

In a first embodiment, the inventive composition comprises 1-amino-4-methylpiperazine as sole component b).

The concentration of 1-amino-4-methylpiperazine of the inventive composition is of up to 3% by weight, preferably of up to 1% by weight, based on the total weight of the composition. Preferably, the concentration of 1-amino-4-methylpiperazine in the inventive composition is 0.1 to 3% by weight, more preferably 0.1 to 2% by weight, especially 0.1 to 1% by weight, based on the total weight of the composition.

In a preferred embodiment, the concentration of 1-amino-4-methylpiperazine in the inventive composition is of 0.1 to 2% by weight, based on a composition comprising 40 to 50% by weight of component a).

In a more preferred embodiment, the total concentration of 1-amino-4-methylpiperazine and prestabilizing compounds is at the most 3% by weight, based on the total weight of the inventive composition.

In a second embodiment, the inventive composition comprises 1,2-diaminopropane as sole component b).

The concentration of component b), 1,2-diaminopropane, in the inventive composition is of up to 3% by weight, preferably of up to 1% by weight, based on the total weight of the composition. Preferably, the concentration of 1,2-diaminopropane in the inventive composition is of 0.1 to 3% by weight, more preferably of 0.1 to 2%, especially 0.1 to 1% by weight, based on the total weight of the composition.

In a preferred embodiment, the concentration in particular of 1,2-diaminopropane in the inventive composition is of 0.5 to 2% by weight, based on a composition comprising 40 to 50% by weight component a).

In a more preferred embodiment, the total concentration of 1,2-diaminopropane and prestabilizing compound is at the most 3% by weight, based on the total weight of the composition.

In a third embodiment, the inventive composition comprises as component b) a mixture of 1-amino-4-methylpiperazine and 1,2-diaminopropane.

The concentration of component b), in particular of the mixture of 1-amino-4-methylpiperazine and 1,2-diaminopropane, in the inventive composition is of up to 3% by weight, preferably of up to 1% by weight, based on the total weight of the composition.

Preferably, the concentration of the mixture of 1-amino-4-methylpiperazine and 1,2-diaminopropane in the inventive composition is of 0.1 to 3% by weight, more preferably of 0.1 to 2%, especially 0.5 to 1.5% by weight, more especially 0.5 to 1% by weight based on the total weight of the composition.

More preferably, the weight ratio of 1-amino-4-methylpiperazine to 1,2-diaminopropane in the inventive composition is in the range of 1:9 to 9:1, in particular 1:9 to 5:1, especially of 1:9 to 4:6.

In a preferred embodiment, the concentration of the mixture of 1-amino-4-methylpiperazine and 1,2-diaminopropane in the inventive composition is of 0.5 to 1.5% by weight, based on a composition comprising 40 to 50% by weight component a).

In a more preferred embodiment, the total concentration of component b) and prestabilizing compound is at the most of 3% by weight, based on the total weight of the composition.

In a fourth embodiment, the inventive composition further comprises at least one component c). Component c) is selected from the group consisting of N,N-diethylhydroxylamine, diethylentriamine, ethylenediamine, hydroxylamine and hydroxylamine salts. Suitable hydroxylamine salts are selected from hydroxylamine sulfate, hydroxylamine chloride and hydroxylamine acetate.

The concentration of component c) of the inventive composition comprises 0 to 3% by weight, preferably 0.1% by weight to 2% by weight, preferably 0.1% by weight to 1% by weight, based on the total weight of the composition.

In a preferred embodiment, the inventive composition comprises 1-amino-4-methylpiperazine as sole component b) and component c). Preferably, component c) is N,N-diethylhydroxylamine.

Preferably, the weight ratio of 1-amino-4-methylpiperazine to component c) is in the range of 1:9 to 9:1, in particular 1:9 to 5:1, especially of 1:9 to 4:6.

Preferably, the inventive composition comprises 1-amino-4-methylpiperazine as sole component b) and N,N-diethylhydroxylamine as sole component c).

Preferably, the weight ratio of 1-amino-4-methylpiperazine to N,N-diethylhydroxylamine is in the range of 1:9 to 9:1, in particular 1:9 to 5:1, especially of 1:9 to 4:6.

In a fifth embodiment, the inventive composition further comprises at least one component d). Component d) is selected from the group consisting of tert-butylcatechol and 4-methoxyphenol, preferably tert-butylcatechol.

The concentration of component d) of the inventive composition, preferably according to the first, second, third or fourth embodiment, comprises 0% by weight to 1% by weight, preferably 0.005 to 0.1% by weight, preferably 0.01 to 0.05% by weight, based on the total weight of the composition. Preferably, the concentration of tert-butylcatechol of the inventive composition comprises 0% by weight to 1% by weight, preferably 0.005 to 0.1% by weight, preferably 0.01 to 0.05% by weight, based on the total weight of the composition.

In a sixth embodiment, the inventive composition, preferably according to the first, second, third, fourth or fifth embodiment comprises further a component e), which is different from component c) and component d). Component e) is selected from the group consisting of film forming amines, corrosion inhibitors, defoamers and/or antifoams, demusifiers, antifoulants or mixtures thereof.

Suitable film forming amines are selected from substituted and unsubstituted alkylimidazolines, fatty amines, fatty oligoamines, alkylsarcosines and mixtures thereof.

Suitable alkylimidazolines are selected from (hydroxy-$C_1$-$C_4$-alkyl)-($C_1$-$C_4$-alkyl)-imidazolines, preferably, (hydroxy-$C_1$-$C_4$-alkyl)-(ethyl)-imidazolines, (hydroxy-$C_1$-$C_4$-alkyl)-(hydroxy-$C_1$-$C_4$-alkyl)-imidazolines, (mono- and di-amino-$C_1$-$C_4$-alkylamino)-($C_1$-$C_4$-alkyl)-imidazolines, (mono- and di-amino-$C_1$-$C_4$-alkylamino)-(mono- and di-amino-$C_1$-$C_4$-alkyl)-imidazolines, (mono- and di-amino-$C_1$-$C_4$-alkylamino)-(hydroxyl-$C_1$-$C_4$-alkyl)-imidazolines, (hydroxyl-$C_1$-$C_4$-alkylamino)-(mono- and di-amino-$C_1$-$C_4$-alkyl)-imidazolines, ($C_1$-$C_4$-alkyl)-($C_1$-$C_4$-alkyl) imidazolines, ($C_1$-$C_4$-alkyl)-imidazolines and mixtures thereof.

Suitable fatty amines and oligoamines are selected from octadecylamine, oleylamine, tallowamine, N-oleyl-1,3-diaminoethane, N-tallow-1,3-diaminopropane, 1-cocoalkyl-1,3-diaminopropane, stearyl-1,3-diaminopropane, N-[3-(cocoalkylamino)propyl]propane-1,3-diamine (=cocoalkyldipropylentriamine), N-[3-(tallowalkylamino)propyl]propane-1,3-diamine (=tallowalkyldipropylentriamine), N-[3-[3-(cocoalkylamino)propylamino]propyl]propane-1,3-diamine (=cocoalkyltripropylentetramine) and N-[3-[3-(tallowalkylamino)propyl-amino]propyl]propane-1,3-diamine (=tallowalkyltripropylentetramine). Suitable amines are commercially available, e.g. the Duomeen(trade mark) brands of AkzoNobel, such as Duomeen(trade mark) T, Duomeen(trade mark) O and Duomeen(trade mark) C, the Triameen(trade mark) brands of AkzoNobel, such as Triameen(trade mark) T and Triameen(trade mark) C, the Dinoram(trade mark) brands of Archem, such as Dinoram (trade mark) O, and Inipol(trade mark) DS, Tetrameen(trade mark) brands of AkzoNobel, such as Tetrameen(trade mark) T.

Suitable alkylsarcosinates are selected from unsaturated and saturated $C_6$-$C_{24}$ alkyl sarcosine, in particular oleyl sarcosine, tallow sarcosine and mixtures thereof.

Suitable corrosion inhibitors are selected from alkylamines, alkanolamines, alkylphosphates, phosphonates and mixtures thereof.

Suitable alkylamines are selected from mono-($C_3$-$C_8$-)alkylamines, di-($C_2$-$C_8$-) alkylamines, tri-($C_2$-$C_8$-)alkylamines, $C_1$-$C_4$-alkoxy-$C_1$-$C_4$-alkylamines and mixtures thereof. Preferred alkylamines are selected from diethylamine, trimethylamine, din-propylamine, trimethylamine, 1-methoxy-3-propylamine and mixtures thereof.

Suitable alkanolamines are selected from monoethanolamine, diethanolamin, triethanolamin, N,N-dimethylaminoethanol, 2-diethylaminoethanol and mixtures thereof.

Suitable alkylphosphates are selected from linear or branched $C_4$-$C_{18}$ alkyl phosphates, preferably from linear or branched $C_6$-$C_{12}$ alkyl phosphates.

Suitable phosphonates are selected from aminotrimethylenephosphonic acid (ATMP), Hydroxyethyldiphosphonic acid (HEDP) and 2-Phosphonobutane-1,2, 4-tricarboxylic acid (PBTC) and mixtures thereof.

Suitable defoamers and/or antifoams are selected from silicon oils, fatty acids and blends of fatty acids with hydrocarbons, homo- and copolymers of ethylene oxide and propylene oxide and mixtures thereof, in particular polypyleneglycol. Silicon oils are preferably used in form of an emulsion.

Suitable silicon oils are selected from polydimethylsiloxane. The polydimethylsiloxane has a molecular weight in the range of 500 to 100 000 g/mol. Preferred are emulsions of polydimethylsiloxanes.

Suitable demusifiers include, are selected from anionic or nonionic surfactants, alkoxylated amines or oligoamines, alkoxylated phenolic resins and mixtures thereof.

Suitable anionic surfactants are selected from $C_6$-$C_{30}$-alkylsulfates, $C_6$-$C_{30}$-alkylethersulfates, $C_6$-$C_{30}$-alkylbenzenesulfonates and mixtures thereof.

Suitable nonionic surfactants are selected from fatty alcohol alkoxylates and copolymers of ethylene oxide and propylene oxide as well as fatty amine alkoxylates and mixtures thereof.

Suitable oligoamines are selected from tetraethylenetriamine (TETA) and higher homologues.

Suitable alkoxylated phenolic resins are selected from phenolic methylene resin alkoxylates.

Suitable antifoulants are selected from polyisobutylenesuccinimide or polyisobutylenesuccinic esters or derivatives thereof and mixtures thereof.

In a preferred embodiment, the inventive composition comprises 5 to 60% by weight, preferably 20 to 60% by weight, of component a), based on the total weight of the composition, 0.1 to 3% by weight, preferably 0.1 to 2% by weight, especially 0.1 to 1% by weight of 1-amino-4-methylpiperazine as component b), based on the total weight of the composition, 0 to 3% by weight, preferably 0 to 2% by weight, especially 0 to 1% by weight of component c) as defined above, based on the total weight of the composition, preferably N,N-diethylhydroxylamine, 0 to 0.3% by weight, preferably 0 to 0.05% by weight of component d) as defined above, based on the total weight of the composition, 0 to 70% by weight, preferably 0 to 30% by weight of component e) as defined above, based on the total weight of the composition, provided that the total weight of component b) and component c) is at the most of 3% by weight, based on the total weight of the composition. If component c) is present it is used in an amount of 0.1 to 3% by weight, preferably 0.1 to 2% by weight, especially 0.1 to 1% by weight, based on the total weight of the composition.

In another preferred embodiment, the inventive composition comprises 5 to 60% by weight, preferably 20 to 60% by weight of component a), based on the total weight of the composition, 0.1 to 3% by weight, preferably 0.1 to 2% by weight, especially 0.1 to 1% by weight of 1,2-diaminopropane as component b), based on the total weight of the composition, 0 to 3% by weight, preferably 0 to 2% by weight, especially 0 to 1% by weight of component c) as defined above, based on the total weight of the composition, preferably N,N-diethylhydroxylamine, 0 to 0.3% by weight, preferably 0 to 0.05% by weight of component d) as defined above, based on the total weight of the composition, 0 to 70% by weight, preferably 0 to 30% by weight of component e) as defined above, based on the total weight of the composition, provided that the total weight of component b) and component c) is at the most of 3% by weight, based on the total weight of the composition.

In another preferred embodiment, the inventive composition comprises 5 to 60% by weight, preferably 20 to 60% by weight of component a), based on the total weight of the composition, 0.1 to 3% by weight, preferably 0.1 to 2% by weight, especially 0.5 to 1.5% by weight of a mixture of 1-amino-4-methylpiperazine and 1,2-diaminopropane as component b), based on the total weight of the composition, 0 to 3% by weight, preferably 0 to 2% by weight, especially 0 to 1% by weight of component c) as defined above, based on the total weight of the composition, preferably N,N-diethylhydroxylamine, 0 to 0.3% by weight, preferably 0 to 0.05% by weight of component d) as defined above, based on the total weight of the composition, 0 to 70% by weight, preferably 0 to 30% by weight of component e) as defined above, based on the total weight of the composition, provided that the total weight of component b) and component c) is at the most of 3% by weight, based on the total weight of the composition.

In another special embodiment of the invention, a composition comprises a) a quaternary trialkylalkanolamine, preferably N,N,N-trimethyl-hydroxyethyl-ammonium hydroxide and b) a mixture of ethylenediamine and N,N-diethylhydroxylamine.

The concentration of component a) of the said composition is preferably of 5 to 60% by weight, more preferably of 20 to 60% by weight, especially 40-50% by weight, based on the total weight of the composition.

Preferably, the concentration of the mixture of ethylenediamine and N,N-diethylhydroxylamine of the said composition is of 0.1 to 3% by weight, more preferably of 0.1 to 2%, especially 0.5 to 1.5% by weight, based on the total weight of the composition.

More preferably, the weight ratio of ethylenediamine to N,N-diethylhydroxylamine is in the range of 1:9 to 9:1, especially of 1:9 to 4:6.

In a preferred embodiment, the concentration of the mixture of ethylenediamine and N,N-diethylhydroxylamine of the said composition is of 0.5 to 1.5% by weight, based on a composition comprising 40 to 50% by weight of component a).

In a more preferred embodiment, the total concentration of component b) and prestabilizing compound is at the most 3% by weight, based on the total weight of the composition.

Further, said composition may comprise at least one component d) as defined above, wherein tert-butylcatechol is preferred.

The concentration of component d) of said composition is 0% by weight to 1% by weight, preferably 0.005 to 0.1% by weight, preferably 0.01 to 0.05% by weight, based on the total weight of the composition. Preferably, the concentration of tert-butylcatechol of the inventive composition is 0% by weight to 1% by weight, preferably 0.005 to 0.1% by weight, preferably 0.01 to 0.05% by weight, based on the total weight of the composition.

Further, said composition may comprise at least one component e) as defined above.

In a preferred embodiment said composition comprises 5 to 60% by weight, preferably 20 to 60% by weight of component a), based on the total weight of the composition, 0.1 to 3% by weight, preferably 0.1 to 2% by weight, especially 0.1 to 1% by weight of a mixture of ethylenediamine and N,N-diethylhydroxylamine as component b), based on the total weight of the composition, 0 to 0.3% by weight, preferably 0 to 0.05% by weight of component d) as defined above, based on the total weight of the composition, 0 to 70% by weight, preferably 0 to 30% by weight of component e) as defined above, based on the total weight of the composition, with the proviso that the total weight of component b) and prestabilizing components is at the most of 3% by weight, based on the total weight of the composition.

The invention also relates to a method for providing the inventive composition comprising component a) and component b) as defined above and optionally component c), d) and/or e) as defined above.

Generally, component b) can be added as poststabilizers by any means suitable to the prestabilized composition comprising component a) obtained from the market. Suitable mixing methods are known by a skilled person, e. g. stirring, shaking, recirculation or simple diffusion (given enough time). While it is not necessary to add the component b) very soon after the production process, it is of course advantageous to do so in order to achieve optimum results. Preferably, component b) is added latest 12 months after the formation of the prestabilized composition comprising component a), more preferably latest 6 months after the formation of the prestabilized composition comprising component a) and most preferably latest 1 month after the formation of the prestabilized composition comprising component a).

Further, as mentioned above, component b) can be used as prestabilizers before/during/after the formation of component a).

Component b) of the present invention may be added to any composition comprising component a) available on the worldwide market, being prestabilized by any of the means described in the prior art. Component b) may also be added to less concentrated composition comprising component a) to effect additional protection. In this case, lower concentrations of component b) will be needed.

The method for stabilizing a composition comprising component a) in particular comprises the following steps i) providing a composition comprising component a) and optionally prestabilizing compounds, ii) adding component b) as defined above to the composition provided in step i) to obtain the inventive composition, iii) optionally adding component c) as defined above to the inventive composition obtained in step ii), iv) optionally adding component d) as defined above to the inventive composition obtained in step ii), or step iii), v) optionally adding component e) as defined above to the inventive composition obtained in step iii), or step iv).

A further embodiment of the invention is the use of the inventive composition for preventing fouling or scaling or corrosion in technical process suffering from fouling or scaling or corrosion.

The invention relates to the use of the inventive composition for preventing fouling or scaling or corrosion in oil refinery or petrochemical processes in particular for preventing fouling or scaling or corrosion of metal parts. The fouling or scaling or corrosion processes may be caused by ammonium salts, such as ammonium chloride and/or ammonium sulfides.

Typical areas for fouling and corrosion are, for example, feed-effluent exchangers of hydrotreater reactor and distillation columns, recycle gas compressors transporting hydrogen, stabilizer, reboiler and overhead sections of distillation equipment.

A further embodiment of the invention is the use of the inventive composition for preventing fouling or scaling or corrosion in water cycle/steam cycle plants.

A further embodiment of the invention is the use of the inventive composition as a basic process chemical in processes requiring the presence of a strong organic base.

A further embodiment of the invention is the use of the inventive composition, where the process requiring the presence of a strong organic base is the preparation of electronics, where the composition is used as a positive photoresist developing agent, as an anisotropic etching agent or as a washing agent for silicon wafers.

A further embodiment of the invention is a method for stabilizing a quaternary trialkylalkanolamine hydroxide which comprises adding a component b) as above to a composition of a quaternary trialkylalkanolamine hydroxide.

A further embodiment of the invention is the use of a component b) as defined above for stabilizing a composition of a quaternary trialkylalkanolamine hydroxide.

The present invention will be further detailed by the following examples, without being restricted in any way to their scope.

EXAMPLES

Abbreviations
1A4MP 1-Amino-4-methylpiperazine
CMR carcinogen, mutagen, reprotoxic (properties)
DAP 1,2-Diaminopropane
DEHA N,N-diethylhydroxylamine
DETA diethylenetriamine
EDA Ethylenediamine
HA hydroxylamine
HAS hydroxylamine sulfate
ID inner diameter
MEHQ 4-Methoxyphenol, Hydrochinonmonomethylether
TBC tertbutylcatechol
Cholin hydroxide N,N,N-trimethyl-hydroxyethyl-ammonium hydroxide <Test Method and Analytics>

A composition (A) comprising choline hydroxide from Balchem Italia Srl was used. The composition had a nominal active choline hydroxide content of 45% by weight and was prestabilized on the manufacturer's factory site by addition of ≤1 w % EDA, according to the manufacturer's specification.

Further, a composition (B) comprising choline hydroxide from Japan Finechem Company, INC. was used in addition to the European base material (having been prestabilized by EDA). The composition had a nominal active choline hydroxide content of 47% by weight and was prestabilized on the manufacturer's factory site by addition of about 800 ppm of hydrazine, according to manufacturer specifications.

Aliquots of this base material were filled into 125 ml glass bottles (Schott, Germany), closed with tightly sealing caps and exposed to 3 different storage conditions, room temperature (meaning about 20-24° C. with some fluctuations), 40° C. and 60° C. for prolonged periods of time. Untreated aliquots served as blank values. Other samples of the same batch were treated with various amounts of the stabilizers and stabilizer combinations and handled exactly in the same way. About once per week, all samples of a certain series were opened, small quantities of these samples filled into 2.5 cm ID glass cuvettes and the APHA (Hazen) color number measured on a Hach Lange DR 3900 spectrophotometer at 455 nm. The color number gave a quantitative value for the degree of discoloration according to the following scheme:

good: <100
fair: 100<X<250
unacceptable >500

The linear range of the method was found to end around values of 500. Hence, samples having exceeded this number once were not measured anymore, but still visually evaluated. After measurement, the measured quantities were filled back into their respective bottles for further storage. Thorough rinsing procedures were applied to minimize cross contamination and waste, such that 100 ml samples were enough for multiple evaluations over the course of several weeks. No inert gas blanketing was used at all, simulating regular air exposure. This corresponds to typical storage conditions of process chemicals on refinery and petrochemical sites, where product containers are often left breathing to the atmosphere without further precautions.

In addition to APHA color measurements, the samples were also evaluated visually, checking for phase separation, turbidity or other unwanted changes.

Storage at 40° C. and 60° C. was performed in temperature controlled heating cabinets.

Example 1: Test of Single Compounds at 40° C.

An untreated composition (A) and samples treated with 1% by weight of single poststabilizers were subjected to the method described above. Test temperature was 40° C. The following results listed in table 1 to table 3 were obtained.

TABLE 1

| Day | Compound (A) untreated (comparative) |
|---|---|
| 0 | 0 |
| 7 | 90 |
| 14 | 203 |
| 21 | 366 |
| 28 | 548 |

TABLE 2

| Day | (A) + 1% EDA | (A) + 1% DEHA |
|---|---|---|
| 0 | 0 | 0 |
| 6 | 26 | 45 |
| 13 | 38 | 70 |
| 20 | 111 | 127 |
| 28 | 196 | 172 |
| 34 | 257 | 205 |

TABLE 2-continued

| Day | (A) + 1% EDA | (A) + 1% DEHA |
|---|---|---|
| 42 | 365 | 279 |
| 48 | 502 | 354 |
| 62 | — | 543 |

TABLE 3

| Day | (A) + 1% DAP | (A) + 1% 1A4MP |
|---|---|---|
| 0 | 15 | 25 |
| 6 | 20 | 44 |
| 13 | 32 | 111 |
| 20 | 53 | 200 |
| 27 | 102 | 340 |
| 34 | 130 | 382 |
| 41 | 199 | 514 |
| 48 | 396 | |
| 76 | 785 | |

The following is concluded from table 1 to table 3:

The composition (A) untreated with postabilizing compounds (base material) is insufficiently stabilized for use at higher temperature as it develops unacceptable color within 25 days.

Example 2: Test of Single Compounds at 60° C.

The test of example 1 was repeated at 60° C. and the following results obtained, listed in tables 4 and 5:

TABLE 4

| Day | Compound (A) untreated (comparative) | (A) + 1% EDA | (A) + 1% DEHA |
|---|---|---|---|
| 0 | 0 | 0 | 0 |
| 7 | 1814 | 304 | 412 |
| 15 | | 1060 | 568 |

TABLE 5

| Day | (A) + 1% DAP | (A) + 1% 1A4MP |
|---|---|---|
| 0 | 25 | 25 |
| 6 | 50 | 278 |
| 13 | 126 | 918 |
| 20 | 411 | — |
| 27 | 512 | — |

The following is concluded from table 4 and 5:

The Color formation is dramatically accelerated at higher temperatures such as 60° C.

The composition (A) (base material) develops unacceptable color at 60° C. within just a few days.

Example 3: Test of EDA and DEHA Combinations at 40° C.

The test of example 1 was repeated using various mixtures of EDA and DEHA over the entire ratio range from 1:9 to 9:1. The following results were obtained and listed in table 6.

TABLE 6

(total concentration of poststabilizer 1% by weight, based on the composition)

| [%] EDA | [%] DEHA | 10 Days | 18 Days | 25 Days | 31 Days | 38 Days | 45 Days | 52 Days | 59 Days | 66 Days | 73 Days | 80 Days |
|---|---|---|---|---|---|---|---|---|---|---|---|---|
| 0 | 100 | 12 | 24 | 28 | 46 | 60 | 79 | 102 | 149 | 183 | 246 | 299 |
| 10 | 90 | 9 | 17 | 17 | 23 | 45 | 57 | 60 | 89 | 120 | 157 | 206 |
| 20 | 80 | 3 | 12 | 15 | 20 | 32 | 48 | 63 | 85 | 121 | 156 | 200 |
| 30 | 70 | 6 | 12 | 13 | 20 | 29 | 39 | 54 | 79 | 98 | 128 | 157 |
| 40 | 60 | 6 | 8 | 13 | 16 | 25 | 32 | 41 | 64 | 86 | 113 | 143 |
| 50 | 50 | 3 | 6 | 7 | 15 | 23 | 27 | 29 | 51 | 74 | 104 | 179 |
| 60 | 40 | 6 | 7 | 9 | 15 | 23 | 29 | 33 | 50 | 76 | 89 | 113 |
| 70 | 30 | 1 | 2 | 10 | 17 | 18 | 26 | 38 | 58 | 86 | 137 | 256 |
| 80 | 20 | 1 | 6 | 7 | 13 | 19 | 39 | 46 | 111 | 186 | 348 | 548 |
| 90 | 10 | 1 | 9 | 16 | 25 | 52 | 114 | 188 | 373 | 481 | 728 | 728 |
| 100 | 0 | 30 | 79 | 166 | 266 | 424 | 614 | 614 | 614 | 614 | 750 | 750 |

The following is concluded from table 6:

The poststabilizers EDA and DEHA exhibit a beneficial effect over the entire ratio range from 1:9 to 9:1, as the color values obtained with any mixture remain lower than the color values obtained with the pure compounds.

Example 4: Test of EDA and DEHA Combinations at 60° C.

Example 3 was repeated, changing the temperature to 60° C. The following results were obtained and listed in table 7.

TABLE 7

(total concentration of poststabilizer 1% by weight, based on the composition)

| [%] EDA | [%] DEHA | 10 Days | 18 Days | 25 Days | 31 Days | 38 Days |
|---|---|---|---|---|---|---|
| 0 | 100 | 125 | 214 | 299 | 380 | 505 |
| 10 | 90 | 82 | 141 | 234 | 330 | 485 |
| 20 | 80 | 58 | 118 | 181 | 265 | 380 |
| 30 | 70 | 49 | 100 | 166 | 250 | 343 |
| 40 | 60 | 42 | 86 | 135 | 200 | 297 |
| 50 | 50 | 37 | 77 | 113 | 168 | 265 |
| 60 | 40 | 28 | 66 | 109 | 163 | 279 |
| 70 | 30 | 27 | 58 | 100 | 157 | 367 |
| 80 | 20 | 24 | 56 | 122 | 285 | 1032 |
| 90 | 10 | 34 | 105 | 349 | 998 | — |
| 100 | 0 | 279 | 935 | 935 | — | — |

The following is concluded from table 7:

The beneficial effect between EDA and DEHA also occurs at 60° C.

Example 5: Test of 1A4MP and DEHA Combinations at 40° C.

The test series of example 3 was repeated, exchanging EDA by 1A4MP, keeping all other conditions unchanged. The following results were obtained and listed in table 8.

TABLE 8

(total concentration of poststabilizer 1% by weight, based on the composition)

| [%] 1A4MP | [%] DEHA | 0 Day | 3 Day | 10 Day | 17 Day | 24 Day | 52 Day | 61 Day | 66 Day | 73 Day | 80 Day | 90 Day | 94 Day |
|---|---|---|---|---|---|---|---|---|---|---|---|---|---|
| 0 | 100 | 20 | 61 | 84 | 148 | 252 | 417 | 582 | — | — | — | — | — |
| 10 | 90 | 20 | 52 | 62 | 100 | 159 | 275 | 309 | 358 | 415 | 519 | — | — |
| 20 | 80 | 20 | 51 | 58 | 93 | 127 | 223 | 267 | 304 | 334 | 424 | 495 | 589 |
| 30 | 70 | 20 | 51 | 63 | 72 | 105 | 170 | 196 | 229 | 245 | 313 | 412 | 457 |
| 40 | 60 | 20 | 48 | 50 | 70 | 105 | 155 | 195 | 210 | 247 | 312 | 400 | 453 |
| 50 | 50 | 20 | 49 | 55 | 67 | 98 | 155 | 177 | 197 | 225 | 292 | 362 | 420 |
| 60 | 40 | 20 | 42 | 45 | 57 | 91 | 126 | 147 | 166 | 193 | 253 | 335 | 387 |
| 70 | 30 | 20 | 43 | 46 | 60 | 91 | 140 | 174 | 204 | 268 | 450 | 781 | — |
| 80 | 20 | 20 | 42 | 43 | 57 | 90 | 172 | 259 | 365 | 534 | — | — | — |
| 90 | 10 | 20 | 33 | 37 | 50 | 84 | 170 | 274 | 377 | 541 | — | — | — |
| 100 | 0 | 20 | 38 | 60 | 148 | 296 | 752 | — | — | — | — | — | — |

The following is concluded from table 8:

The poststabilizers 1A4MP and DEHA exhibit a beneficial effect over the entire ratio range from 1:9 to 9:1, as the color values obtained with any mixture remain lower than the color values obtained with the pure compounds.

Example 6: Test of 1A4MP and DEHA Combinations at 60° C.

The test series of example 5 was repeated changing the temperature to 60° C. and keeping all other conditions the same. The following results were obtained and listed in table 9.

TABLE 9

(total concentration of poststabilizer 1% by weight, based on the composition)

| [%] 1A4MP | [%] DEHA | 0 Day | 3 Day | 10 Day | 17 Day | 24 Day |
|---|---|---|---|---|---|---|
| 0 | 100 | 20 | 601 | 950 | | |
| 10 | 90 | 20 | 456 | 665 | | |
| 20 | 80 | 20 | 290 | 522 | | |
| 30 | 70 | 20 | 205 | 450 | 546 | |
| 40 | 60 | 20 | 127 | 306 | 432 | 515 |
| 50 | 50 | 20 | 133 | 295 | 431 | 550 |
| 60 | 40 | 20 | 95 | 204 | 328 | 560 |
| 70 | 30 | 20 | 87 | 175 | 266 | 410 |
| 80 | 20 | 20 | 88 | 216 | 369 | 750 |
| 90 | 10 | 20 | 77 | 210 | 344 | 641 |
| 100 | 0 | 20 | 170 | 803 | | |

The following is concluded from table 9:

The beneficial effect between 1A4MP and DEHA also occurs at 60° C.

Example 7: Test of 1A4MP and DAP Combinations at 40° C.

The test series of example 3 was repeated, using combinations of 1A4MP and DAP, keeping all other parameters the same. The following results were obtained and listed in table 10:

TABLE 10

(total concentration of poststabilizer 1% by weight, based on the composition).

| [%] 1A4MP | [%] DAP | 0 Day | 3 Day | 10 Day | 17 Day | 24 Day | 52 Day | 61 Day | 66 Day | 73 Day | 80 Day | 90 Day | 94 Day |
|---|---|---|---|---|---|---|---|---|---|---|---|---|---|
| 0 | 100 | 20 | 26 | 27 | 54 | 82 | 274 | 377 | 492 | 452 | | | |
| 10 | 90 | 20 | 22 | 24 | 31 | 56 | 113 | 135 | 171 | 216 | 330 | 469 | 529 |
| 20 | 80 | 20 | 26 | 28 | 45 | 78 | 183 | 232 | 300 | 410 | 620 | | |
| 30 | 70 | 20 | 25 | 29 | 54 | 85 | 196 | 271 | 346 | 479 | 755 | | |
| 40 | 60 | 20 | 30 | 35 | 55 | 85 | 180 | 234 | 286 | 387 | 584 | | |
| 50 | 50 | 20 | 31 | 35 | 64 | 111 | 284 | 350 | 453 | 613 | | | |
| 60 | 40 | 20 | 28 | 39 | 89 | 168 | 438 | 632 | | | | | |
| 70 | 30 | 20 | 35 | 47 | 98 | 183 | 504 | | | | | | |
| 80 | 20 | 20 | 27 | 55 | 142 | 229 | 583 | | | | | | |
| 90 | 10 | 20 | 36 | 51 | 118 | 229 | 610 | | | | | | |
| 100 | 0 | 20 | 38 | 60 | 148 | 296 | 752 | | | | | | |

The following is concluded from table 10:

The poststabilizers 1A4MP and DAP exhibit a beneficial effect over the entire ratio range from 1:9 to 9:1, as the color values obtained with any mixture remain lower than the color values obtained with the pure compounds.

Example 8: Test of 1A4MP and DAP Combinations at 60° C.

The test series of example 7 was repeated changing the temperature to 60° C. and keeping all other parameters the same. The following results were obtained and listed in table 11.

TABLE 11

(total concentration of poststabilizer 1% by weight, based on the composition).

| [%] 1A4MP | [%] DAP | 0 Day | 3 Day | 10 Day | 17 Day | 24 Day |
|---|---|---|---|---|---|---|
| 0 | 100 | 20 | 81 | 205 | 533 | |
| 10 | 90 | 20 | 52 | 194 | 539 | |
| 20 | 80 | 20 | 49 | 186 | 339 | 831 |
| 30 | 70 | 20 | 73 | 210 | 629 | |
| 40 | 60 | 20 | 70 | 277 | 863 | |
| 50 | 50 | 20 | 82 | 276 | 760 | |
| 60 | 40 | 20 | 110 | 336 | 693 | |
| 70 | 30 | 20 | 143 | 486 | 1080 | |
| 80 | 20 | 20 | 131 | 457 | 1039 | |
| 90 | 10 | 20 | 132 | 547 | | |
| 100 | 0 | 20 | 170 | 803 | | |

The following is concluded from table 11:

The beneficial effect between 1A4MP and DAP also occurs at 60° C.

Summing up the results presented in examples 1-8 it can be concluded that the Composition (A) is not sufficiently stabilized for use at higher temperatures and that the poststabilizer compounds EDA, DAP, DEHA and 1A4MP exhibit efficiency at these temperatures. It can be further concluded that 3 poststabilizer combinations exist, namely EDA-DEHA, 1A4MP-DEHA and 1A4MP-DAP, which exhibit beneficial properties.

Example 9: Test of Single Compounds at 40° C.

The test of example 1 was repeated, wherein composition (B) is used instead of composition (A). The results are listed in table 12.

Example 10: Test of Single Compounds at 60° C.

The test of example 9 was repeated, at 60° C. and the following results obtained. The results are listed in table 13.

TABLE 12

40° C.

| Day | (B)* | (B) + DAP 1% | (B) + 1A4MP 1% | (B) + DAP 0.9% + 1A4MP 0.1% | (B) + EDA 1% | (B) + DAP 0.3% + 1A4MP 0.7% | (B) + DAP 0.5% + 1A4MP 0.5% | (B) + DAP 0.7 + 1A4% MP 0.3% | (B) + DEHA 1% |
|---|---|---|---|---|---|---|---|---|---|
| 0  | 30  | 30   | 30  | 30  | 30  | 30  | 30  | 30  | 30  |
| 8  | 659 | 37   | 54  | 36  | 51  | 42  | 39  | 37  | 95  |
| 14 |     | 55   | 87  | 41  | 105 | 52  | 44  | 49  | 134 |
| 24 |     | 74   | 100 | 47  | 126 | 70  | 54  | 55  | 175 |
| 28 |     | 105  | 137 | 64  | 178 | 71  | 65  | 66  | 227 |
| 35 |     | 334  | 191 | 101 | 215 | 98  | 104 | 77  | 341 |
| 42 |     | 1500 | 398 | 130 | 305 | 157 | 119 | 109 | 542 |
| 56 |     |      | 860 | 356 | 747 | 448 | 232 | 345 |     |
| 63 |     |      |     | 570 |     | 870 | 360 | 500 |     |
| 70 |     |      |     |     |     |     | 660 |     |     |

| Day | (B) + DEHA 0.3% + 1A4MP 0.7% | (B) + DEHA 0.3% + EDA 0.7% | (B) + DEHA 0.5% + 1A4MP 0.5% | (B) + DEHA 0.7% + 1A4MP 0.3% | (B) + DEHA 0.4% + 1A4MP 0.6% | (B) + DEHA 0.5% + EDA 0.5% | (B) + DEHA 0.7% + EDA 0.3% |
|---|---|---|---|---|---|---|---|
| 0  | 30  | 30  | 30  | 30  | 30  | 30  | 30  |
| 8  | 54  | 57  | 60  | 75  | 57  | 60  | 74  |
| 14 | 58  | 85  | 67  | 97  | 70  | 76  | 91  |
| 24 | 87  | 92  | 90  | 145 | 88  | 85  | 123 |
| 28 | 119 | 106 | 110 | 161 | 106 | 115 | 167 |
| 35 | 125 | 133 | 132 | 199 | 133 | 208 | 216 |
| 42 | 150 | 164 | 159 | 238 | 162 | 163 | 221 |
| 56 | 194 | 217 | 227 | 367 | 225 | 199 | 319 |
| 63 | 257 | 277 | 303 | 457 | 291 | 238 | 427 |
| 70 | 328 | 306 | 413 | 668 | 388 | 295 | 610 |

*(comparative)

TABLE 13

60° C.

| Day | (B)* | (B) + DAP 1% | (B) + 1A4MP 1% | (B) + DAP 0.9% + 1A4MP 0.1% | (B) + EDA 1% | (B) + DAP 0.3% + 1A4MP 0.7% | (B) + DAP 0.5% + 1A4MP 0.5% | (B) + DAP 0.7% + 1A4MP 0.3% | (B) + DEHA 1% |
|---|---|---|---|---|---|---|---|---|---|
| 0  | 30   | 30  | 30  | 30  | 30   | 30  | 30  | 30  | 30  |
| 8  | 1062 | 36  | 85  | 31  | 172  | 51  | 41  | 33  | 200 |
| 14 |      | 95  | 528 | 101 | 1164 | 189 | 92  | 94  | 420 |
| 24 |      | 950 |     | 854 |      | 865 | 823 | 732 | 753 |
| 28 |      |     |     |     |      |     |     |     |     |

| Day | (B) + DEHA 0.3% + 1A4MP 0.7% | (B) + DEHA 0.3% + EDA 0.7% | (B) + DEHA 0.5% + 1A4MP 0.5% | (B) + DEHA 0.7% + 1A4MP 0.3% | (B) + DEHA 0.4% + 1A4MP 0.6% | (B) + DEHA 0.5% + EDA 0.5% | (B) + DEHA 0.7% + EDA 0.3% |
|---|---|---|---|---|---|---|---|
| 0  | 30  | 30  | 30  | 30  | 30  | 30  | 30  |
| 8  | 82  | 85  | 95  | 129 | 81  | 106 | 133 |
| 14 | 147 | 189 | 165 | 244 | 221 | 193 | 270 |
| 24 | 271 | 346 | 357 | 510 | 311 | 461 | 610 |
| 28 | 460 | 538 | 567 |     | 497 | 676 |     |

*(comparative)

The following is concluded from tables 12 and 13: The poststabilizers DAP and 1A4MP are also effective in choline hydroxide solutions prestabilized by other compounds such as hydrazine. It can be further concluded that 3 poststabilizer combinations exist, namely EDA-DEHA, 1A4MP-DEHA and 1A4MP-DAP, which exhibit beneficial properties also in choline hydroxide solutions prestabilized by hydrazine.

Test series carried out at room temperature confirmed the results although color development was by far slower and found less critical.

The invention claimed is:

1. A composition comprising a) a quarternary trialkylalkanolamine hydroxide and b) at least one diamine as component b), which is selected from the group consisting of 1-amino-4-methylpiperazine and a mixture of 1-amino-4-methylpiperazine and 1,2-diaminopropane.

2. The composition according to claim 1, wherein component b) is 1-amino-4-methylpiperazine.

3. The composition according to claim 1, wherein component b) is the mixture of 1-amino-4-methylpiperazine and 1,2-diaminopropane.

4. The composition according to claim 3, wherein the weight ratio of 1-amino-4-methylpiperazine to 1,2-diaminopropane is in the range of 1:9 to 9:1, preferably of 1:9 to 4:6.

5. The composition according to claim 1, wherein the component a) is N,N,N-trimethyl-hydroxyethyl-ammonium hydroxide.

6. The composition according to claim 1, wherein the concentration of component a) is in the range of 5 to 60% by weight, preferably in the range of 20 to 60% by weight, based on the total weight of the composition.

7. The composition according to claim 1, wherein the concentration of component b) is in the range of 0.1 to 3% by weight, preferably in the range of 0.1 to 1% by weight, based on the total weight of the composition.

8. The composition according to claim 1, which is an aqueous composition.

9. The composition according to claim 1, further comprising at least one component c) selected from the group consisting of N,N-diethylhydroxylamine, diethylentriamine, ethylenediamine, hydroxylamine or hydroxylamine salts.

10. The composition according to claim 9, comprising 1-amino-4-methylpiperazine and N,N-diethylhydroxylamine.

11. The composition according to claim 10, wherein the weight ratio of 1-amino-4-methylpiperazine to N,N-diethylhydroxylamine is in the range of 1:9 to 9:1, preferably 4:6 to 6:4.

12. The composition according to claim 1, further comprising at least one component d) selected from the group consisting of tert-butylcatechol and 4-methoxyphenol.

13. The composition according to claim 12, wherein the concentration of tert-butylcatechol is in the range of 0.005% by weight to 0.1% by weight, preferably in the range of 0.01% by weight to 0.05% by weight, based on the total weight of the composition.

14. The composition according to claim 1 further comprising at least one component e), which is different from component c) or d), which is selected from film forming amines, corrosion inhibitors, defoamers and/or antifoams, demusifiers, antifoulants and mixtures thereof.

\* \* \* \* \*